US008497087B2

(12) United States Patent
Tsujimoto et al.

(10) Patent No.: US 8,497,087 B2
(45) Date of Patent: *Jul. 30, 2013

(54) METHOD FOR PRODUCING TARGET SUBSTANCE BY FERMENTATION

(75) Inventors: Nobuharu Tsujimoto, Kawasaki (JP); Tomoko Suzuki, Kawasaki (JP); Hisao Ito, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 489 days.

This patent is subject to a terminal disclaimer.

(21) Appl. No.: 11/275,900

(22) Filed: Feb. 2, 2006

(65) Prior Publication Data

US 2006/0205043 A1    Sep. 14, 2006

Related U.S. Application Data

(63) Continuation of application No. 10/121,693, filed on Apr. 15, 2002, now Pat. No. 7,097,999.

(30) Foreign Application Priority Data

May 2, 2001    (JP) ................. 2001-135517

(51) Int. Cl.
| | | |
|---|---|---|
| C12P 1/00 | (2006.01) | |
| C12P 13/04 | (2006.01) | |
| C12P 13/22 | (2006.01) | |
| C12P 13/08 | (2006.01) | |
| C12N 1/21 | (2006.01) | |

(52) U.S. Cl.
USPC ............. 435/41; 435/106; 435/108; 435/115; 435/252.33

(58) Field of Classification Search
USPC ................. 435/41, 106, 108, 115, 252.33
See application file for complete search history.

(56) References Cited

U.S. PATENT DOCUMENTS

| | | | |
|---|---|---|---|
| 4,346,170 A | 8/1982 | Sano et al. | |
| 4,687,742 A | 8/1987 | Skoet et al. | |
| 4,970,157 A | 11/1990 | Hibino et al. | |
| 5,015,582 A | 5/1991 | Hibino et al. | |
| 5,175,107 A | 12/1992 | Debabov et al. | |
| 5,179,011 A | 1/1993 | Kishimoto et al. | |
| 5,508,047 A | 4/1996 | Domingues | |
| 6,171,845 B1 | 1/2001 | Elischweski et al. | |
| 7,097,999 B2 * | 8/2006 | Tsujimoto et al. ............. | 435/41 |

FOREIGN PATENT DOCUMENTS

| | | |
|---|---|---|
| EP | 0488424 | 6/1992 |
| EP | 1001027 | 5/2000 |
| JP | 60-047692 | 3/1985 |
| JP | 61-212285 | 9/1986 |
| JP | 63-157986 | 6/1988 |
| JP | 03-277269 | 12/1991 |
| JP | 95-11406 | 11/1997 |
| WO | WO 90/04636 | 5/1990 |
| WO | WO01/12833 | 2/2001 |

OTHER PUBLICATIONS

Burkovski, A., et al., "Glutamate excretion in *Escherichia coli*: dependency on the *relA* and *spoT* genotype," Arch. Microbiol. 1995;164:24-28.
Lin, E. C. C., "Dissimilatory Pathways for Sugars, Polyols, and Carboxylates," *Escherichia coli* abd *Salmonella*, 2$^{nd}$ Ed., vol. 1, 1996, pp. 307-308, ASM Press, Washington, DC, US.
Munro, G. F., et al., "Dependence of the Putrescine Content of *Escherichia coli* on the Osmotic Strength of the Medium," J. Biol. Chem. 1972;247(4):1272-1280.
Schlegel, H. G., "Allgemeine Mikrobiologie," 7$^{th}$ ed., 1992, pp. 310-311 and 372, Georg Thieme Verlag Stuttgart, New York, US, with English translation.
Thimann, K. V., "Kapitel XIV, Die Ameisensäuregärung," Das Leben Der Bakterien. 1964, pp. 493-495, VEB Gistav Fischer Verlag, with English translation.
Notice of Opposition for EP Patent No. 1254957 (Sep. 21, 2006).
Communication of a Notice of Opposition from the EPO for EP Patent No. 1254957 (Oct. 13, 2006).
Dean, D. A., et al., "Regulation of the Maltose Transport System of *Escherichia coli* by the Glucose-Specific Enzyme III of the Phosphoenolpyruvate-Sugar Phosphotransferase System," J. Biol. Chem. 1990;265(34):21005-21010.
Ehrmann, et al., "Identification of Endogenous Inducers of the mal Region in *Escherichia coli*," J. Bacteriol. 1987; 169(8):3539-3545.
Kuhnau, S., et al., "The Activities of the *Escherichia coli* Malk Protein in Maltose Transport, Regulation, and Inducer Exclusion Can be Separated by Mutations," J. Bacteriol. 1991;173(7):2180-2186.
Monod, J., et al., "The Phenomenon of Enzymatic Adaptation and its Bearings on Problems of Genetics and Cellular Differentiation," Growth 1947;11:223-289.
Postma, P. W., et al., "Phosphoenolpyruvate Carbohydrate Phosphotransferase Systems," *Escherichia coli* and *Salmonella* Cellular and Molecular Biology, Second Edition, vol. 1, pp. 1149-1174, 1996.
Zeng, G. Q., et al., "Mutational Analysis of the Enzyme III$^{Glc}$ the Phosphoenolpyruvate Phosphotransferase System in *Escherichia coli*," Res. Microbiol. 1992;143:251-261.
Lippincott, J., et al., "MalFGK Complex Assembly and Transport and Regulatory Characteristics of MalK Insertion Mutants," J. Bacteriol. 1997;179(4):1337-1343.
Grounds of Appeal Action from European Patent App. No. 02008316.8 (Jan. 14, 2009).

(Continued)

*Primary Examiner* — Anand Desai
*Assistant Examiner* — Iqbal H Chowdhury
(74) *Attorney, Agent, or Firm* — Shelly Guest Cermak; Cermak Nakajima LLP

(57) ABSTRACT

A method for producing a target substance by utilizing a microorganism by culturing the microorganism in a medium to produce and accumulate the target substance in the medium and collecting the target substance from the culture is described. The microorganism is a mutant recombinant strain in which maltose assimilation is controlled by reducing or eliminating the interaction between IIA$^{Glc}$ protein of the glucose PTS and a protein involved in non-PTS uptake of maltose.

5 Claims, 1 Drawing Sheet

OTHER PUBLICATIONS

Notice of Reason for Rejection for Japanese Patent App. No. 2001-135517 (Aug. 17, 2010) with English translation thereof.

Final Decision of Rejection from Japanese Patent App. No. 2001-135517 (Feb. 8, 2011) with English translation thereof.

Zeng, G. Q., et al., "Mutational Analysis of the Enzyme III$^{Glc}$ of the Phosphoenolpyruvate Phosphotransferase System in *Escherichia coli*," Res. Microbiol. 1992;143:251-261.

* cited by examiner

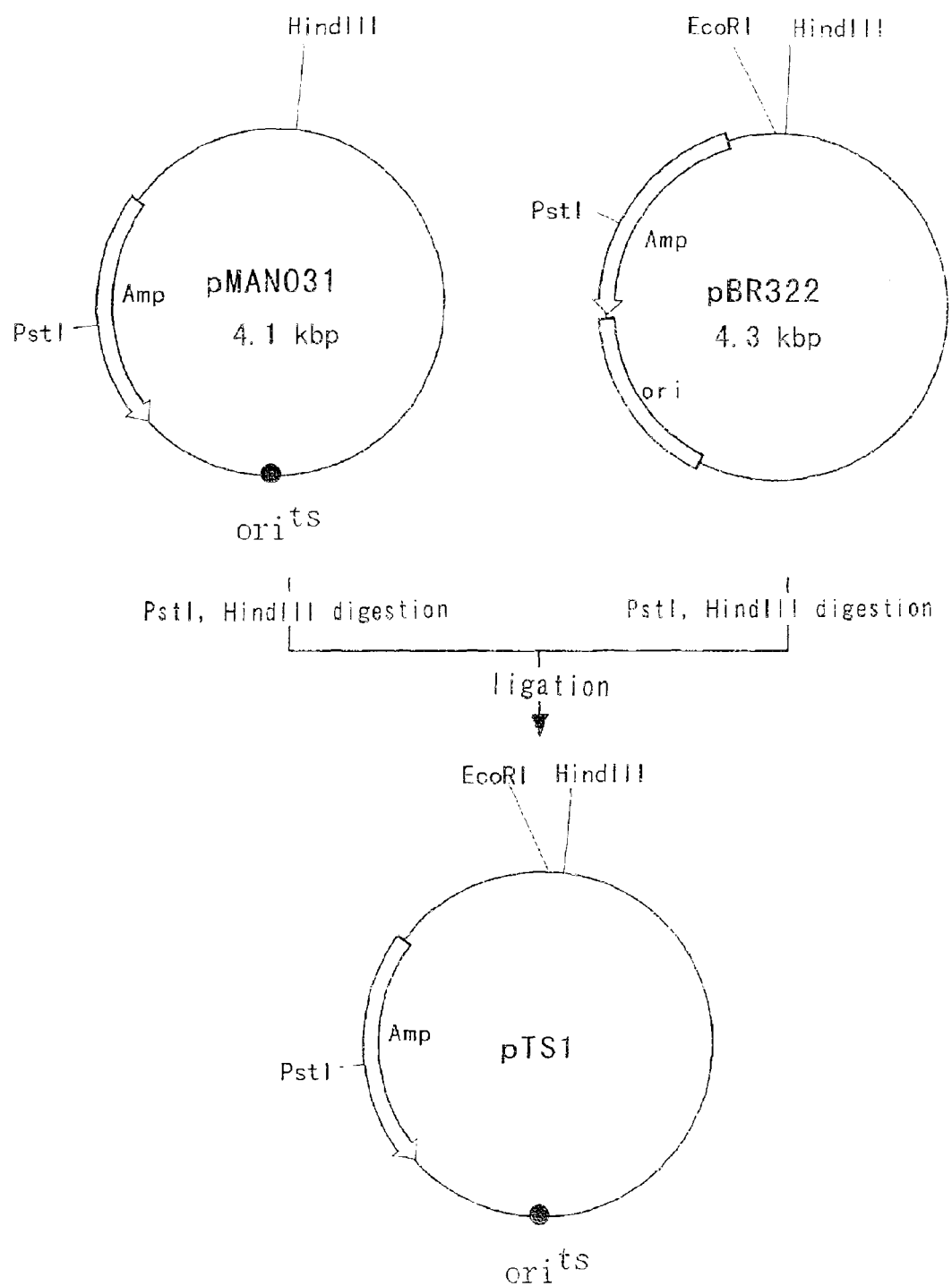

SEQUENCE LISTING

<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: Artificial DNA

<400> SEQUENCE: 1
ggcggtaatg tggagatgcg cacataaaat cgcc        34

<210> SEQ ID NO 2
<211> LENGTH: 39
<212> TYPE: DNA
<213> ORGANISM: Artificial Sequence
<220> FEATURE:
<223> OTHER INFORMATION: Artificial DNA

<400> SEQUENCE: 2
cctgagtcat tgcttttctt ttttcacatc acctgtgac        39

<210> SEQ ID NO 3
<211> LENGTH: 35
<212> TYPE: DNA
<213> ORGANISM: Artificial Sequence
<220> FEATURE:
<223> OTHER INFORMATION: Artificial DNA

<400> SEQUENCE: 3
cggaagtgct acaactgacg catttgctgg atcgc        35

<210> SEQ ID NO 4
<211> LENGTH: 35
<212> TYPE: DNA
<213> ORGANISM: Artificial Sequence
<220> FEATURE:
<223> OTHER INFORMATION: Artificial DNA

<400> SEQUENCE: 4
gcgatccagc aaatgcgtca gttgtagcac ttccg        35

<210> SEQ ID NO 5

-continued

```
<211> LENGTH: 34
<212> TYPE: DNA
<213> ORGANISM: Artificial Sequence
<220> FEATURE:
<223> OTHER INFORMATION: Artificial DNA

<400> SEQUENCE: 5
gatttcttta gtatcggcac caatgattta acgc                              34

<210> SEQ ID NO 6
<211> LENGTH: 30
<212> TYPE: DNA
<213> ORGANISM: Artificial Sequence
<220> FEATURE:
<223> OTHER INFORMATION: Artificial DNA

<400> SEQUENCE: 6
aaattgccgc gatctagaca gtgccattgc                                   30

<210> SEQ ID NO 7
<211> LENGTH: 40
<212> TYPE: DNA
<213> ORGANISM: Artificial Sequence
<220> FEATURE:
<223> OTHER INFORMATION: Artificial DNA

<400> SEQUENCE: 7
gaaaccaacc acacattctc tatcgaatct gatagcggcg                        40

<210> SEQ ID NO 8
<211> LENGTH: 40
<212> TYPE: DNA
<213> ORGANISM: Artificial Sequence
<220> FEATURE:
<223> OTHER INFORMATION: Artificial DNA

<400> SEQUENCE: 8
cgccgctatc agattcgata gagaatgtgt ggttggtttc                        40
```

METHOD FOR PRODUCING TARGET SUBSTANCE BY FERMENTATION

This application claims priority under 35 U.S.C. §119 to Japanese Patent Application No. 2001-135517, filed May 2, 2001, and is a continuation under 35 U.S.C. §120 of Ser. No. 10/121,693, filed Apr. 15, 2002, now U.S. Pat. No. 7,097,999 the entirety of which is incorporated by reference. Also, the Sequence Listing on compact disk filed May 5, 2005 in parent application Ser. No. 10/121,693 is hereby incorporated by reference (File name: 221916US0.txt; File size: 2 KB; Date recorded: May 4, 2005).

BACKGROUND OF THE INVENTION

1. Field of the Invention

The present invention relates to a method for producing a target substance using a microorganism. More precisely, the present invention provides a means for improving production of L-amino acids, antibiotics, vitamins, growth factors and bioactive substances using a microorganism.

2. Brief Description of the Background Art

Typical methods for producing substances using microorganisms are known, including methods for producing L-amino acids by fermentation. L-amino acids are used not only as seasonings and foodstuffs, but also as components of various nutritional mixtures for medical purposes. Furthermore, they are used as additives for animal feed, reagents in the drug manufacturing and chemical industries, and growth factors for production of L-amino acids such as L-lysine and L-homoserine using a microorganism. Known microorganisms that can produce L-amino acids by fermentation include the coryneform bacteria, *Escherichia* bacteria, *Bacillus* bacteria, *Serratia* bacteria, and so forth.

During production of target substances by fermentation such as described above, most of the raw materials are known to contain saccharides such as blackstrap molasses. Also, in amino acid or nucleic acid fermentation, the culture is performed using a saccharide as a raw material. Although sugarcane contains abundant amounts of starch, it is rare to use it as a raw material. It is more commonly used as a decomposition product, resulting in, for example, monosaccharides or disaccharides. In these methods, a solution of a saccharide-producing enzyme such as amylase is generally used, and thereby polysaccharide starches are decomposed into relatively low molecular weight saccharides such as glucose, maltose, and maltotriose.

During fermentation of Gram-negative enterobacteria such as *Escherichia coli* (*E. coli*), the use of a starch decomposition solution can cause problems. For example, *E. coli* consumes glucose when it is present as the main component, but it suffers from so-called glucose repression, which means that oligosaccharides containing two or more monosaccharides such as maltose are consumed only after monosaccharides are completely consumed. Therefore, if fermentation is terminated when only glucose, present as the main component of the starch decomposition solution, is consumed, oligosaccharides such as maltose are not assimilated but remain. Furthermore, if the intent is to consume oligosaccharides after consumption of glucose, the culture time must be extended, and therefore utility cost and so forth are wasted.

It is known that *E. coli* and *Salmonella typhimurium* generally suffer from glucose repression. That is, when glucose is assimilated with other carbon sources such as lactose, maltose and glycerol, glucose is assimilated first and the other carbon sources are assimilated later. Monod et al. discovered that, when lactose and glucose were the carbon sources, two-phase proliferation, i.e., so-called diauxie, was observed (Monod, J., Growth, 11, 223-247, 1947). Through research in molecular biology, the mechanism thereof has become clear. That is, IIA$^{Glc}$ (glucose PTS enzyme II) acts as a phosphate donor for glucose in the phosphate cascade at the time of assimilation in the glucose-phosphoenolpyruvate-sugar phosphotransferase system, i.e., the so-called PTS system, and exists in a dephosphorylated state. The dephosphorylated IIA$^{Glc}$ causes so-called inducer exclusion, in which the dephosphorylated IIA$^{Glc}$ inhibits uptake of the other saccharides (Postma P. W., Lengeler J. W. and Jacobson G. R.: in *Escherichia coli* and *Salmonella*: Cellular and Molecular Biology (ed. Neidhardt F. C.), pp. 1149-1174, 1996, ASM Press, Washington D.C.).

Uptake of maltose in *E. coli* suffers from glucose repression caused by the interaction between the dephosphorylated IIA$^{Glc}$ and the MalK protein, which constitutes the uptake system for maltose by non-PTS. That is, when the bacterium is taking up glucose, IIA$^{Glc}$ exists in excessive amounts in the cell and binds to the MalK protein, resulting in inhibition of maltose uptake. Furthermore, a mutant strain which has improved maltose uptake in the presence of a glucose analogue was also obtained, and this mutant strain has a mutation in the malK gene coding for the MalK protein (Dean D. A. et al., Regulation of the Maltose Transport System of *Escherichia coli* by the Glucose-specific Enzyme III of the Phosphoenolpyruvate-Sugar Phosphotransferase System., J. Biol. Chem., 265 (34), 21005-21010, 1990; Kuhnau, S. et al., The Activities of the *Escherichia coli* MalK Protein in Maltose Transport and Regulation, and Inducer Exclusion Can Be Separated by Mutations, J. Bacteriol., 173 (7), 2180-2186, 1991).

Furthermore, and also for IIA$^{Glc}$, a mutant strain that contained a mutant protein which showed reduced binding with lactose permease has been reported (Zeng, G. A. et al., Mutation analysis of the enzyme IIIGlc of the phosphoenolpyruvate phosphotransferease system in *Escherichia coli*, Res. Microbiol., 143, 251-261, 1992). Lactose permease is an uptake enzyme for lactose, which is a non-PTS saccharide.

However, whether the aforementioned mutant strains can assimilate maltose simultaneously in the presence of glucose has not been reported.

SUMMARY OF THE INVENTION

An object of the present invention is to improve the assimilation ability of a microorganism for oligosaccharides, in particular, maltose, during production of a substance by fermentation of the microorganism. A carbon source containing glucose and oligosaccharides is used in the fermentation, such as a starch decomposition solution.

A microorganism is described in which the interaction between the glucose PTS IIA$^{Glc}$ protein and a protein involved in non-PTS uptake of maltose was reduced or eliminated and wherein the microorganism could assimilate maltose even in the presence of glucose.

It is an object of the present invention to provide a method for producing a target substance utilizing a microorganism comprising culturing the microorganism in a medium and collecting the target substance from the culture, wherein the microorganism controls maltose assimilation by reducing or eliminating the interaction between the glucose PTS IIA$^{Glc}$ protein and a protein involved in non-PTS uptake of maltose, and wherein said microorganism can take up glucose and maltose.

It is a further object of the present invention to provide the method as described above, wherein the protein involved in the non-PTS uptake of maltose is a maltose carrier protein which is able to decompose ATP.

It is a further object of the present invention to provide the method as described above, wherein the protein is MalK.

It is a further object of the present invention to provide the method as described above, wherein the MalK protein has a mutation selected from the group consisting of substituting a Thr residue for the Ala residue at position 124 and substituting a Gln residue for the Leu residue at position 327.

It is a further object of the present invention to provide the method as described above, wherein the IIA$^{Glc}$ protein has a mutation selected from the group consisting of substituting a Ser residue for the Gly residue at position 47 and substituting a Thr residue for the Ala residue at position 76.

It is a further object of the present invention to provide the method as described above, wherein the target substance is an L-amino acid.

It is a further object of the present invention to provide the method as described above, wherein the target substance is selected from the group consisting of L-lysine, L-threonine, and L-phenylalanine.

It is a further object of the present invention to provide the method as described above, wherein the microorganism is an *Escherichia* bacterium.

According to the present invention, the ability of a microorganism to assimilate an oligosaccharide, in particular, maltose, can be improved during production of a substance by fermentation with a carbon source containing glucose and an oligosaccharide such as starch decomposition solution.

BRIEF DESCRIPTION OF THE DRAWINGS

FIG. 1 shows the structure of the plasmid vector pTS1 having a temperature-sensitive replication origin.

DETAILED DESCRIPTION OF EXEMPLARY EMBODIMENTS

The target substance which is produced according to the present invention may be selected from various L-amino acids including, for example, L-threonine, L-lysine, L-glutamic acid, L-leucine, L-isoleucine, L-valine, L-phenylalanine, and so forth. Particularly preferred L-amino acids are L-lysine, L-threonine, and L-phenylalanine. In addition, the target substance may be any substance that has been produced in a conventional manner by microorganisms using a medium containing glucose and an oligosaccharide such as maltose as carbon sources, and may be a nucleic acid such as guanylic acid and inosinic acid, vitamins, antibiotics, growth factors, bioactive substances, or the like. The present invention can of course include the use of other substances, so long as the substances require a carbon source in the biosynthesis thereof, even if they are not currently known to be produced using a microorganism.

The microorganism used in the present invention is a microorganism in which maltose assimilation is controlled by the interaction between the glucose PTS IIA$^{Glc}$ protein and a protein involved in non-PTS uptake of maltose. Specifically, bacteria belonging to the group of enterobacteria such as *Escherichia, Enterobacter, Klebsiella*, coryneform, *Bacillus, Serratia*, and so forth may be used in the present invention. Preferably a microorganism that allows gene substitution may be used. Whether a microorganism can be used for the present invention or not can be determined by, for example, observing the growth of a wild-type strain of the microorganism in a medium containing glucose and maltose as carbon sources, and confirming if two-phase proliferation, i.e., the so-called diauxie, occurs or not. If diauxie occurs, this is evidence that maltose assimilation is controlled by the interaction of the glucose PTS IIA$^{Glc}$ protein and a protein involved in the non-PTS uptake of maltose.

Specific examples of microorganisms that can be used for the present invention include, for example, *Escherichia coli* AJ11442 (NRRL B-12185 and FERM BP-1543, U.S. Pat. No. 4,346,170), *Brevibacterium lactofermentum* AJ3990 (ATCC31269, U.S. Pat. No. 4,066,501) etc. if L-lysine is the target substance, *Escherichia coli* VKPM B-3996 (RIA1867, U.S. Pat. No. 5,175,107), *Corynebacterium acetoacidophilum* AJ12318 (FERM BP-1172, U.S. Pat. No. 5,188,949) etc. for L-threonine, *Escherichia coli* AJ12604 (FERM BP-3579, European Patent Publication No. 488,424), *Brevibacterium lactofermentum* AJ12637 (FERM BP-4160, French Patent Publication No. 2,686,898) etc. for L-phenylalanine, *Escherichia coli* AJ12624 (FERM BP-3853, French Patent Publication No. 2,680,178), *Brevibacterium lactofermentum* AJ12475 (FERMBP-2922, U.S. Pat. No. 5,272,067) etc. for L-glutamic acid, *Escherichia coli* AJ11478 (FERM P-5274, Japanese Patent Publication (Kokoku) No. 62-34397), *Brevibacterium lactofermentum* AJ3718 (FERM P-2516, U.S. Pat. No. 3,970,519) etc. for L-leucine, *Escherichia coli* KX141 (VKPM B-4781, European Patent Publication No. 519,113), *Brevibacterium flavum* AJ12149 (FERM BP-759, U.S. Pat. No. 4,656,135) etc. for L-isoleucine, *Escherichia coli* VL1970 (VKPM B-4411, European Patent Publication No. 519,113), *Brevibacterium lactofermentum* AJ12341 (FERM BP-1763, U.S. Pat. No. 5,188,948) etc. for L-valine, and so forth.

Furthermore, when the target substance is L-lysine, L-threonine, or L-phenylalanine, strains obtained by introducing pVIC40, pCABD2, or pMGAL1 into *E. coli* W3100 (tyrA), and which also contain a gene involved in the production of each of these amino acids, can also be suitably used, and they are described in the examples herein.

Furthermore, the activity of a protein involved in the production of the target substance may be enhanced in the microorganism of the present invention, or the activity of a protein involved in decomposition, or the like, of the target substance may be reduced in the microorganism of the present invention, depending on the target substance.

The microorganism of the present invention is a mutant strain or recombinant strain obtained or derived from such parent microorganisms as described above, in which the interaction between the glucose PTS IIA$^{Glc}$ protein and a protein involved in non-PTS uptake of maltose is reduced or eliminated, but the mutant or recombinant microorganism can also take up glucose and maltose. That is, in the present invention, the IIA$^{Glc}$ protein and the protein involved in non-PTS uptake of maltose both contain a mutation that does not substantially affect the uptake of glucose and maltose, but does reduce or eliminate the interaction between these two proteins.

In *Escherichia coli*, the IIA$^{Glc}$ protein is encoded by the crr gene. The MalK protein, which is encoded by malK gene in *Escherichia coli*, is an example of a protein involved in the non-PTS uptake of maltose.

In order to reduce or eliminate the interaction of the IIA$^{Glc}$ protein and the protein involved in non-PTS uptake of maltose, a mutation that reduces or eliminates the interaction between these proteins can be introduced into one or both genes coding for these proteins.

The crr gene or malK gene that has a mutation as mentioned above can be obtained by, for example, isolating the crr gene or malK gene from a strain that can grow in a medium containing maltose as a carbon source and a glucose analogue such as 2-deoxyglucose. As a mutant-type malK gene that can be obtained as described above, a mutant malK gene whereby the Ala residue at position 124 is substituted by a Thr residue of the MalK protein (A124T mutation) has been reported (Dean, D. A. et al., J. Biol. Chem., 265 (34), 21005-21010, 1990; Kuhnau, S. et al., J. Bacteriol., 173 (7), 2180-2186, 1991). Furthermore, a mutant malK gene encoding the MalK protein, whereby the Leu residue at position 327 is substituted for a Gln residue (L327Q mutation), which was obtained by the inventors of the present invention, can also be suitably used for the present invention. Furthermore, a mutant malK gene encoding a mutant MalK protein which has both mutations, A124T and L327Q, can also be used for the present invention.

The mutant crr gene of the present invention includes a mutant crr gene whereby the Gly residue at position 47 is substituted with a Ser residue in the encoded $IIA^{Glc}$ protein, or whereby the Ala residue at position 76 is substituted with a Thr residue, or both of these mutations.

The positions of the aforementioned mutations are determined from the Met residue corresponding to the initiation codon, which is counted as the first codon. In addition, the malK gene or crr gene may contain one or more mutations other than the mutations according to the present invention, and hence deletion, substitution, or insertion of one or more amino acid residues may occur in the encoded MalK protein or $IIA^{Glc}$ protein. Even such a malK gene or crr gene may be used for the present invention, so long as the interaction between the MalK protein and $IIA^{Glc}$ protein is reduced or eliminated, and the uptake of glucose and maltose is not substantially affected. When the MalK protein or $IIA^{Glc}$ protein contains a deletion or insertion of one or more amino acid residues, the positions of the aforementioned mutations will change. For example, if the MalK protein has a deletion of one amino acid residue on the N-terminus side of the 327th Leu residue, the 327th Leu residue would become the 326th residue. Even in this case, the 326th Leu residue would correspond to the 327th Leu residue of a wild-type protein. Therefore, in the present specification, the positions of mutations shall represent positions corresponding to the positions in the wild-type gene or wild-type protein.

To introduce the aforementioned mutations into the malK gene and/or crr gene, site-specific mutagenesis or the like can be used, and/or the mutant gene for malK gene and/or crr gene can be substituted on the chromosome of the microorganism via gene substitution utilizing homologous recombination.

Gene substitution can be performed, for example, using a temperature-sensitive plasmid as described herein. Examples of temperature-sensitive plasmids from *Escherichia coli* include pMAN031 (J. Bacteriol., 162, 1196, 1985), pMAN997 (WO99/03988), and so forth. These plasmids can autonomously replicate in *Escherichia coli* at least at 30° C., but cannot autonomously replicate at 37-42° C.

Furthermore, a strain having a target mutation in the malK gene and/or crr gene can also be obtained by treating the microorganism with UV irradiation or a commonly-used mutagenizing agent, such as N-methyl-N'-nitro-N-nitrosoguanidine (NTG) or nitrous acid, and selecting a strain that can grow in a medium containing a glucose analogue, such as 2-deoxyglucose.

Whether a candidate strain is a target mutant strain or not can be confirmed by isolating the malK gene or crr gene from the candidate strain and investigating its nucleotide sequence around the mutation point.

As the medium used for culture of the microorganism of the present invention, conventional well-known media can be chosen depending on the kind of microorganism which is used. That is, media containing a carbon source, nitrogen source, inorganic ions, and other organic components as required can be used. However, it is preferable to use a medium containing glucose and an oligosaccharide, such as maltose, as carbon sources.

As the carbon source other than glucose and maltose, sugars such as lactose, galactose, and starch hydrolysate, alcohols such as glycerol and sorbitol, organic acids such as fumaric acid, citric acid, and succinic acid, and so forth can be used.

As the nitrogen source, inorganic ammonium salts such as ammonium sulfate, ammonium chloride and ammonium phosphate, organic nitrogen such as soybean hydrolysate, ammonia gas, aqueous ammonia, and so forth can be used.

As an organic trace nutrient source, appropriate amounts of required substances such as vitamin $B_1$, L-homoserine, and L-tyrosine, yeast extract, and so forth are preferably in the medium. In addition to these, small amounts of potassium phosphate, magnesium sulfate, iron ions, manganese ions, and so forth are added to the medium as required.

The culture may be performed under well-known conditions that are conventionally used depending on the microorganism to be used. For example, the culture is preferably performed under aerobic conditions for 16-120 hours. The culture temperature is controlled to 25-45° C. and pH is controlled at 5-8 during the culture. Inorganic or organic acidic or alkaline substances as well as ammonia gas and so forth can be used to adjust the pH.

To collect a metabolic product from the medium after completion of the culture, no special method is required for the present invention. That is, collection of the target substance can be attained by a combination of well-known methods such as using an ion exchange resin, precipitation, and others.

EXAMPLES

Hereinafter, the present invention will be explained with reference to the following non-limiting examples. The reagents used in the following examples were obtained from Wako Pure Chemicals or Nakarai Tesque unless otherwise indicated. The compositions of the media used in each example are shown below.

L medium:

| Bacto tryptone peptone (DIFCO) | 10 g/L |
| Yeast extract (DIFCO) | 5 g/L |
| NaCl | 5 g/L |

These were autoclaved at 120° C. for 20 minutes.

L agar medium:
L medium

| Bacto agar (DIFCO) | 15 g/L |

These were steam-sterilized at 120° C. for 20 minutes.

SOC medium:

| Bacto tryptone peptone (DIFCO) | 20 g/L |
| Yeast extract (DIFCO) | 5 g/L |

10 mM NaCl
2.5 mM KCl
10 mM MgSO$_4$
10 mM MgCl$_2$
20 mM Glucose

The components except for magnesium solution and glucose were autoclaved (120° C., 20 minutes), then combined with 2 M magnesium stock solution (1 M MgSO$_4$, 1 M MgCl$_2$) and 2 M glucose solution, which solutions had been preliminarily passed through a 0.22 µm filter, and passed through a 0.22 µm filter again.

M9 minimal medium:

| | |
|---|---|
| Na$_2$HPO$_4$.12H$_2$O | 80 g/L |
| KH$_2$PO$_4$ | 15 g/L |
| NaCl | 2.5 g/L |
| NH$_4$Cl | 5 g/L |
| MgSO$_4$.7H$_2$O | 246.48 mg/L |
| Saccharide (glucose or maltose or mixture of these at a suitable ratio) | 5 g/L | pH 7.0

MgSO$_4$ and glucose were separately sterilized (120° C., 20 minutes) and added. A suitable amount of amino acids and vitamins were added as required. pH was adjusted with NaOH.

M9 minimal agar medium:
M9 minimal medium

| | |
|---|---|
| Bacto agar (DIFCO) | 15 g/L |

Amino acid production medium:

| | |
|---|---|
| (NH$_4$)$_2$SO$_4$ | 20 g/L |
| KH$_2$PO$_4$ | 1 g/L |
| MgSO$_4$.7H$_2$O | 1 g/L |
| FeSO$_4$.7H$_2$O | 10 mg/L |
| MnSO$_4$.4H$_2$O | 10 mg/L |
| Yeast Extract (DIFCO) | 2 g/L |
| Saccharide (glucose or maltose, or mixture of these at a suitable ratio) | 40 g/L |
| L-Tyosine | 100 mg/L |
| CaCO$_3$ (Japanese pharmacopoeia) | 30 g/L |
| Streptomycin | 50 mg/L. |

The saccharide, MgSO$_4$.7H$_2$O, and streptomycin were separately sterilized. The other components were mixed, adjusted to pH 7.0 with KOH and autoclaved at 115° C. for 10 minutes. CaCO$_3$ was subjected to dry sterilization at 180° C. for 2 days. Streptomycin was sterilized by filtration.

Example 1

Introduction of a Mutation into the malK Gene, and Confirmation of Improved Maltose Assimilation A colony of *E. coli* W3100 was inoculated into 5 ml of L medium and cultured overnight with shaking. From the obtained cells, chromosomal DNA was prepared using Wizard Genomic DNA Purification Kit (Promega). PCR was performed using the above chromosomal DNA as a template and the primers shown below.

```
Primer 1:
                                     (SEQ ID NO: 1)
5'-GGCGGTAATGTGGAGATGCGCACATAAAATCGCC-3'

Primer 2:
                                     (SEQ ID NO: 2)
5'-CCTGAGTCATTGCTTTTCTTTTTTCACATCACCTGTGAC-3'
```

PCR was performed using Pyrobest DNA Polymerase (Takara Shuzo) according to the manufacturer's protocol. After completion of the reaction, the amplification product was blunt-ended and phosphorylated using the BKL Kit (Takara Shuzo). The amplified fragment was ligated using the Ligation Kit ver.2 (Takara Shuzo) to pSTV28 (Takara Shuzo), which had been treated with the restriction enzyme Sma I (Takara Shuzo), and then dephosphorylated. This ligation reaction mixture was transformed into *E. coli* JM109 according to the method of Hanahan et al. (Hanahan, D., Studies on transformation of *Escherichia coli* with plamids, J. Mol. Biol., 166, 557-580, 1983). Selection of the transformants was carried out on L agar medium containing 50 µg/ml of chloramphenicol (Cm), 0.2 mM IPTG (Isopropyl-1-thio-β-D-galactopyranoside), and 40 µg/ml of X-gal (5-bromo-4-chloro-3-indolyl-β-D-galactopyranoside). A plasmid was extracted from the transformants in a conventional manner, and the nucleotide sequence of the inserted fragment was determined to confirm that the malK gene was inserted into the Sma I site of pSTV28. This plasmid was designated pSTVmalK.

Nucleotide substitution in the malK gene on pSTVmalK was carried out as follows. It was decided to introduce a substitution of A for G at the 370th position (substitution of Thr for the 124th Ala residue in the MalK protein). The positions in the DNA sequences used herein are numbered from the A of the initiation codon, ATG, which was taken as the first nucleotide, and the positions of amino acid residues are numbered from the Met residue corresponding to the above initiation codon, which was taken as the first amino acid residue.

First, substitution of the nucleotide on the plasmid was performed by using QuickChange™ Site-Directed Mutagenesis Kit (STRATAGENE). The sequences of the primers used for introducing the malK mutation are shown below.

```
Primer 3:
                                     (SEQ ID NO: 3)
5'-CGGAAGTGCTACAACTGACGCATTTGCTGGATCGC-3'

Primer 4:
                                     (SEQ ID NO: 4)
5'-GCGATCCAGCAAATGCGTCAGTTGTAGCACTTCCG-3'
```

Confirmation of the mutation was determined by determining the nucleotide sequence of the objective site according to the protocol with the kit. The produced plasmid was designated pSTVmalK-A124T. The plasmid was digested with restriction enzymes EcoR I and Hind III (Takara Shuzo) and ligated to the same restriction enzyme sites in a plasmid vector pTS 1, which has a temperature-sensitive replication origin.

pTS1 was obtained by exchanging the Pst I-Hind III fragments of pMAN031 (Matsuyama, S. and Mizushima S., Construction and characterization of a deletion mutation lacking micF, a proposed regulatory gene for OmpF synthesis in *Escherichia coli*., J. Bacteriol., 162 (3), 1196-1202, 1985) and pBR322 (Takara Shuzo) (FIG. 1). This plasmid was designated pTSmalK-A124T.

Homologous recombination of the malK gene with malK on the chromosome of E. coli W3100 (tyrA) (see Europe Patent Publication No. 488,424) was conducted according to a usual homologous recombination procedure (Matsuyama, S and Mizushima, S., J. Bacteriol., 162(3), 1196-1202, 1985) by utilizing the temperature sensitivity of the aforementioned plasmid pTSmalK-A124T.

Briefly, E. coli W3 100 (tyrA) was transformed according to the method of Hanahan et al. (J. Mol. Biol., 166, 557-580) using pTSmalK-A124T. A colony which emerged after culture at 30° C. was inoculated into a test tube containing 5 ml of L medium containing 50 μg/ml ampicillin and cultured at 30° C. overnight with shaking. This culture broth was diluted $10^3$ to $10^4$ times, and 0.1 ml of the dilution was applied to L agar medium containing 50 μg/ml of ampicillin and cultured overnight at 42° C. The colony which emerged was inoculated into 5 ml of L medium in a test tube and cultured overnight at 30° C. with shaking. 0.1 ml of this culture broth was inoculated into 5 ml of L medium in a test tube and cultured at 37-42° C. for 3-4 hours with shaking. This culture broth was diluted $10^3$ to $10^7$ times, and 0.1 ml of the dilution was applied to L agar medium and cultured overnight at 37-42° C. The ampicillin sensitivity of the colony which emerged was confirmed.

The mutation point of the target gene-substituted strain was confirmed as follows. PCR was performed using the aforementioned colony as a template and Pyrobest DNA Polymerase. Primer 1 and Primer 2 were used as the primers, and PCR was performed according to the protocol for the enzyme. After completion of the reaction, the reaction mixture was subjected to gel filtration to remove residual primers. The MicroSpin™ S-400HR Column (produced by Amersham Pharmacia Biotech) was used, and the protocol for the column was followed. The obtained PCR product was a mutant-type malK gene of the malK gene-substituted strain. The nucleotide sequence of this gene was determined mainly for the region containing the mutation point. The mutant strain was confirmed to have the desired mutation in the malK gene, and was designated E. coli W3100 (tyrA)malK1.

The growth of E. coli W3100 (tyrA)malK1 in M9 medium containing 0.05% glucose and 0.45% maltose was monitored by OD measurement. E. coli W3100 (tyrA) was used as a control. Although the two-phase proliferation, i.e., the so-called diauxie, was observed for E. coli W3100 (tyrA), such two-phase proliferation was not observed for the malK mutation-introduced strain, E. coli W3100 (tyrA)malK1. That is, due to the introduction of the malK mutation, inducer exclusion did not result, and maltose assimilated simultaneously with glucose assimilation.

Example 2

Introduction of a Mutation into the crr Gene and Confirmation of an Improvement in Maltose Assimilation In this example, a mutation was introduced into the crr gene in order to reduce the interaction between the MalK protein and the crr gene product, $IIA^{Glc}$.

A colony of E. coli W3100 was inoculated into 5 ml of L medium and cultured overnight with shaking. From the obtained cells, chromosomal DNA was prepared using the Wizard Genomic DNA Purification Kit (Promega). PCR was performed using the above chromosomal DNA as a template and the primers shown below.

```
Primer 5:
                                          (SEQ ID NO: 5)
5'-GATTTCTTTAGTATCGGCACCAATGATTTAACGC-3'

Primer 6:
                                          (SEQ ID NO: 6)
5'-AAATTGCCGCGATCTAGACAGTGCCATTGC-3'
```

PCR was performed using Pyrobest DNA Polymerase (Takara Shuzo) and according to the protocol with the enzyme. After completion of the reaction, the amplification product was blunt-ended and phosphorylated using BKL Kit (Takara Shuzo). The amplified fragment was ligated using the Ligation Kit ver.2 (Takara Shuzo) to pMW219 (Nippon Gene) which had been treated with restriction enzyme SmaI (Takara Shuzo) and then dephosphorylated. E. coli JM109 was transformed with this ligation reaction mixture according to the method of Hanahan et al. Selection of the transformants was carried out on L agar medium containing 25 μg/ml of kanamycin (Km), 0.2 mM IPTG (Isopropyl-1-thio-β-D-galactopyranoside) and 40 μg/ml of X-gal (5-bromo-4-chloro-3-indolyl-β-D-galactopyranoside). A plasmid was extracted from the transformants in a conventional manner, and the nucleotide sequence of the inserted fragment was determined to confirm that the crr gene was inserted into the Sma I site of pMW219. This plasmid was designated pMWcrr.

Nucleotide substitution of the crr gene on pMWcrr was carried out as follows. It was decided to introduce the nucleotide substitution of A for G at the 226th position (substitution of Thr for the 76th Ala residue, Zeng, G. A. et al., Mutational analysis of the enzyme $III^{Glc}$ of the phosphoenolpyruvate phosphotransferease system in Escherichia coli., Res. Microbiol., 143, 251-261, 1992). The positions in the DNA sequences used herein are numbered from the A in the initiation codon, ATG, which was taken as the first nucleotide, and the positions of amino acid residues are numbered form the Met residue corresponding to the above initiation codon, which was taken as the first amino acid residue.

First, substitution of the nucleotide on the plasmid was performed using QuickChange™ Site-Directed Mutagenesis Kit (STRATAGENE). The sequences of the primers used for introducing the crr mutation are shown below.

```
Primer 7:
                                          (SEQ ID NO: 7)
5'-GAAACCAACCACACATTCTCTATCGAATCTGATAGCGGCG-3'

Primer 8:
                                          (SEQ ID NO: 8)
5'-CGCCGCTATCAGATTCGATAGAGAATGTGTGGTTGGTTTC-3'
```

The introduction of the mutation was confirmed by determining the nucleotide sequence of the objective site according to the protocol attached to the aforementioned kit. The produced plasmid was designated pMWcrr-A76T. The plasmid was digested with the restriction enzymes EcoR I and Xba I (both produced by Takara Shuzo) and ligated between the same restriction enzyme sites of the plasmid vector pMAN997 (refer to International Patent Publication WO99/03988), which has a temperature-sensitive replication origin.

This plasmid was designated pMANcrr-A76T. Homologous recombination was performed for the crr gene on the E. coli W3100 (tyrA) chromosome using this plasmid by the same method as that used for obtaining the malK mutant strain, and thus a strain having the mutation in the crr gene was obtained.

The mutation point of the target gene-substituted strain was confirmed in the same manner as for the malK mutant strain.

PCR was performed using an ampicillin-resistant colony as a template and Ex Taq Polymerase (Takara Shuzo). Primer 5 and Primer 6 were used as the primers, and PCR was performed according to the protocol with the enzyme. After completion of the reaction, the reaction mixture was subjected to gel filtration to remove residual primers in the reaction mixture. The MicroSpin™ S-400HR Column (Amersham Pharmacia Biotech) was used according to the protocol with the column. The obtained PCR product was a mutant-type crr gene of the crr gene-substituted strain. The nucleotide sequence of this gene was determined mainly for the region containing the mutation point. The mutant strain was confirmed to contain the desired mutation as described above, and was designated *E. coli* W3100 (tyrA)crr3.

The growth of *E. coli* W3100 (tyrA)crr3 in M9 medium containing 0.05% glucose and 0.45% maltose was monitored by OD measurement. *E. coli* W3100 (tyrA) was used as a control. Although the two-phase proliferation, i.e., the so-called diauxie, was observed for *E. coli* W3100 (tyrA), such two-phase proliferation was not observed for the crr mutation-introduced strain, *E. coli* W3100 (tyrA)crr3. That is, due to the introduction of crr mutation, inducer exclusion did not result, and maltose assimilated simultaneously with glucose assimilation. The same event was observed when nucleotide substitution of A for the 139th G (substitution of Ser for the 47th Gly residue) was introduced.

Example 3

Acquisition of Glucose Analogue-Resistant Strain, Identification of the Mutation Point of the Resistant Strain, and Introduction of the Mutation into *E. coli* W3100 (tyrA)

A colony of *E. coli* W3100 (tyrA) was inoculated into a test tube containing 5 ml of L medium and cultured overnight with shaking. The cultured cells were washed twice with 5 ml of physiological saline and suspended in the same volume of physiological saline. 0.1 ml of this suspension was applied to M9 agar medium containing maltose as a carbon source, and the surface was dried. One platinum loop of 2-deoxyglucose was placed on the plate, and the cells were cultured at 37° C. for two or three days. *E. coli* W3100 (tyrA) can utilize maltose as a carbon source, but if a glucose analogue such as 2-deoxyglucose is present, repression occurs, and growth is halted. In this case, a growth inhibition circle forms around the point where the glucose analogue is placed. If culture is performed for two or three days, colonies that are able to grow emerged at a certain frequency within the inhibition circle. Glucose analogue-resistant strains were obtained based on the above phenomenon.

Mutations on the malK gene of malK#1 and malK#2 were investigated among the glucose analogue-resistant strains. The mutation points were confirmed as follows. A colony of each strain was formed, and PCR was performed using the colony as a template and Pyrobest DNA Polymerase. PCR was performed using Primer 1 and Primer 2 as the primers and according to the protocol with the enzyme. After completion of the reaction, the reaction mixture was subjected to gel filtration to remove the residual primers. The MicroSpin™ S-400HR Column (Amersham Pharmacia Biotech) was used according to the protocol with the column. The obtained PCR products were malK genes of the glucose-resistant strains malK#1 and malK#2, and the nucleotide sequences of these genes were determined. As a result, it was found that "A" substituted for the 980th "T" in both strains, and in connection with that, Gln was substituted for the 327th Leu residue. This mutation has not been previously reported, and was designated L327Q type mutation.

The L327Q type mutation was introduced into *E. coli* W3100 (tyrA) by the method described above. The obtained mutation-introduced strain was designated *E. coli* W3100 (tyrA)malK327. In a similar manner, growth of *E. coli* W3100 (tyrA)malK327 in a M9 medium containing 0.05% glucose and 0.45% maltose was monitored by OD measurement. *E. coli* W3100 (tyrA) was used as a control. Although the two-phase proliferation, i.e., the so-called diauxie, was observed for *E. coli* W3100 (tyrA), such two-phase proliferation was not observed for the malK mutation-introduced strain, *E. coli* W3100 (tyrA)malK327. That is, it was found that, because of the introduction of the novel malK mutation, inducer exclusion did not result, and maltose assimilated simultaneously with glucose assimilation.

Example 4

Evaluation of L-amino Acid Productivity of the malK Mutant Strains pVIC40 (WO90/04636), pCABD2 (WO95/16042) and pMGAL1 (Japanese Patent Laid-open Publication (Kokai) No. 5-344881) were each introduced into *E. coli* W3100 (tyrA)malK327, and the ability to produce L-lysine, L-threonine, and L-phenylalanine was investigated for each strain.

Plasmid pVIC40 contains a threonine operon and can be prepared from *E. coli* VKPM B-3996 strain (deposited at USSR Antibiotics Research Institute (VNIIA) with a registration number of RIA1867), which contains the plasmid (WO90/04636).

pCABD2 contains the following DNA sequences: 1) DNA (dapA*24) coding for dihydrodipicolinate synthase (DDPS) derived from *Escherichia coli* and which has a mutation which eliminates feedback inhibition by L-lysine, 2) DNA (lysC*80) coding for aspartokinase III derived from *Escherichia coli* and which has a mutation which eliminates feedback inhibition by L-lysine, 3) DNA (dapB) coding for dihydrodipicolinate reductase derived from *Escherichia coli*, and 4) DNA (ddh) coding for diaminopimelate dehydrogenase derived from *Brevibacterium lactofermentum* (WO95/16042).

pMGAL1 contains a gene coding for 3-deoxy-D-arabino-hepturonate-7-phosphate synthase derived from *Escherichia* bacterium of which feedback inhibition was eliminated, and a gene coding for chorismate mutase-prephenate dehydratase derived from *Escherichia* bacterium of which feedback inhibition is eliminated (Japanese Patent Laid-open Publication No. 5-344881).

*E. coli* W3100 (tyrA)malK327 was transformed with each plasmid by the method of Hanahan et al. Each obtained transformant was inoculated into 5 ml of L medium containing 50 μg/ml of streptomycin and cultured at 37° C. overnight with shaking. Then, 50 μl of the culture broth was applied to L agar medium containing 50 μg/ml of streptomycin and cultured overnight at 37° C. An amino acid production medium containing a mixture of glucose and maltose (36 g/L glucose, 5.8 g/L of maltose) as the carbon source in a volume of 20 ml was introduced into a 500-ml volume Sakaguchi flask, and ⅛ of the cells grown on the aforementioned agar medium was scraped and inoculated into the medium. After completion of the culture, the concentration of each amino acid and the remaining glucose and maltose were quantified. As controls, transformants obtained by introducing each of the plasmids into *E. coli* W3100 (tyrA) were used. The results are shown in Table 1.

TABLE 1

| strain (host/plasmid) | Lys (g/L) | Thr (g/L) | Phe (g/L) | Remained glucose (g/L) | remained maltose (g/L) |
|---|---|---|---|---|---|
| W3110(tyrA)/pRS | 0.00 | 0.00 | 0.91 | 0.0 | 5.8 |
| W3110(tyrA)malK327/pRS | 0.00 | 0.00 | 0.86 | 0.0 | 0.0 |
| W3110(tyrA)/pCABD2 | 9.55 | — | — | 0.0 | 5.6 |
| W3110(tyrA)malK327/pCABD2 | 10.80 | — | — | 0.0 | 0.0 |
| W3110(tyrA)/pVIC40 | — | 8.48 | — | 0.0 | 4.1 |
| W3110(tyrA)malK327/pVIC40 | — | 8.62 | — | 0.0 | 0.0 |
| W3110(tyrA)/pMGAL1 | — | — | 4.57 | 0.0 | 5.7 |
| W3110(tyrA)malK327/pMGAL1 | — | — | 4.69 | 1.2 | 0.0 |

— Not tested,
pRS: vector (initial concentrations of glucose and maltose were 36 g/L and 5.8 g/L, respectively, and culture time was 14 hours)
Lys: lysine;
Thr: threonine;
Phe: phenylalanine When *E. coli* W3100 (tyrA) was used as the host, maltose had not assimilated at the point where the glucose was consumed. On the other hand, when *E. coli* W3100 (tyrA) malK327 was used as the host, the maltose was assimilated within a similar culture time, and thus it was found that consumption of maltose did not suffer from glucose repression.

Furthermore, the *E. coli* W3100 (tyrA)malK327 strains each harboring pVIC40, pCABD2, and pMGAL1 showed improvement in the ability to produce L-lysine, L-threonine and L-phenylalanine compared with the *E. coli* W3 100(tyrA) strains harboring each of the plasmids.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid utilizing a microorganism comprising:
   A) culturing the microorganism in a medium containing both glucose and maltose as carbon sources,
   B) allowing said L-amino acid to accumulate in the medium, and
   C) collecting the L-amino acid from the medium,
   wherein a mutation is introduced into a gene encoding for a protein selected from the group consisting of the glucose PTS IIA$^{Glc}$ protein, MalK, and a combination thereof, and as a result of the mutation(s), the interaction between the glucose PTS IIA$^{Glc}$ protein and MalK is reduced or eliminated in the microorganism as compared to the same microorganism which does not contain the mutation(s), and
   wherein said microorganism can take up glucose and maltose.

2. The method according to claim 1, wherein the MalK protein is from *E. coli* and the mutation is selected from the group consisting of substituting a Thr residue for the Ala residue at position 124 of the MalK protein, substituting a Gln residue for the Leu residue at position 327 of MalK protein, and a combination thereof.

3. The method according to claim 1, wherein the IIA$^{Glc}$ protein is from *E. coli* and the mutation is selected from the group consisting of substituting a Ser residue for the Gly residue at position 47 of the glucose PTS IIA$^{Glc}$ protein, substituting a Thr residue for the Ala residue at position 76 of the glucose PTS IIA$^{Glc}$ protein, and a combination thereof.

4. The method according to claim 1, wherein the L-amino acid is selected from the group consisting of L-lysine, L-threonine, and L-phenylalanine.

5. The method according to claim 1, wherein the microorganism is an *Escherichia* bacterium.

* * * * *